(12) United States Patent
Yang et al.

(10) Patent No.: US 10,160,700 B2
(45) Date of Patent: Dec. 25, 2018

(54) PROCESS AND APPARATUS FOR RECYCLING AND REFINING PROPYLENE

(71) Applicants: CHINA PETROLEUM & CHEMICAL CORPORATION, Beijing (CN); SHANGHAI RESEARCH INSTITUTE OF PETROCHEMICAL TECHNOLOGY SINOPEC, Shanghai (CN)

(72) Inventors: Weisheng Yang, Shanghai (CN); Mujin Li, Shanghai (CN); De Shi, Shanghai (CN); Zhi He, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY SINOPEC, Shanghai (CN)

( * ) Notice: Subject to any disclaimer, the term of this patent is extended or adjusted under 35 U.S.C. 154(b) by 647 days.

(21) Appl. No.: 14/805,840

(22) Filed: Jul. 22, 2015

(65) Prior Publication Data

US 2016/0023965 A1   Jan. 28, 2016

(30) Foreign Application Priority Data

Jul. 24, 2014   (CN) .......................... 2014 1 0355420
Jul. 24, 2014   (CN) .......................... 2014 1 0355936

(51) Int. Cl.
*C07C 7/04*   (2006.01)
*B01D 3/14*   (2006.01)
(Continued)

(52) U.S. Cl.
CPC ................ *C07C 7/04* (2013.01); *B01D 3/007* (2013.01); *B01D 3/148* (2013.01); *B01D 3/26* (2013.01); *C07C 7/005* (2013.01)

(58) Field of Classification Search
CPC ............................................. C07C 7/04–7/09
See application file for complete search history.

(56) References Cited

U.S. PATENT DOCUMENTS 3,632,482 A    1/1972   Hoory et al.
5,274,138 A *  12/1993  Keating ................ C07C 29/132
                                                              549/529

(Continued)

FOREIGN PATENT DOCUMENTS

CN   1505616 A    6/2004
EP   1382601 A1   1/2004
(Continued)

OTHER PUBLICATIONS

Search Report dated Feb. 15, 2016, by the Spanish Patent Office in corresponding Spanish Patent Application No. 201531094 (6 pages).

*Primary Examiner* — Bobby Ramdhanie
*Assistant Examiner* — Briana M Obenhuber
(74) *Attorney, Agent, or Firm* — Buchanan Ingersoll & Rooney PC

(57) ABSTRACT

An apparatus for recycling propylene includes a first propylene recovery column, a flash tank, a second propylene recovery column, and a depropanizing column. The apparatus can effectively solve the problem of high power consumption in the prior art, and can be used for the industrial manufacturing of propylene recovery from a propylene oxide apparatus. A process for recycling and refining propylene also is described.

20 Claims, 1 Drawing Sheet

(51) Int. Cl.
*B01D 3/26* (2006.01)
*C07C 7/00* (2006.01)
*B01D 3/00* (2006.01)

(56) References Cited

U.S. PATENT DOCUMENTS

| | | | |
|---|---|---|---|
| 2004/0133018 A1* | 7/2004 | Oku | C07D 301/14 |
| | | | 549/529 |
| 2005/0085648 A1 | 4/2005 | Tsuji et al. | |
| 2010/0048925 A1* | 2/2010 | Yamamoto | C07D 301/19 |
| | | | 549/529 |
| 2010/0056814 A1* | 3/2010 | Chang | C07D 301/06 |
| | | | 549/518 |

FOREIGN PATENT DOCUMENTS

| | | | |
|---|---|---|---|
| EP | 1420014 A1 * | 5/2004 | C07D 301/19 |
| ES | 2305442 | 11/2008 | |

\* cited by examiner

PROCESS AND APPARATUS FOR RECYCLING AND REFINING PROPYLENE

CROSS REFERENCE TO RELATED APPLICATION

The present application claims benefit of Chinese patent applications 201410355936.6 and 201410355420.1, filed to the Chinese Patent Office on Jul. 24, 2014, which are entirely incorporated herein by reference.

TECHNICAL FIELD

The present disclosure relates to a process and an apparatus for recycling propylene, and in particular to a process and an apparatus for recycling propylene from the products of a propylene epoxidation reaction.

BACKGROUND OF THE INVENTION

Propylene oxide (PO) is very important organic chemical material, which ranks only next to polypropylene and acrylonitrile in yield among propylene derivatives. Propylene oxide is mainly used for preparing polyether, propylene glycol, isopropanolamine, non-polyether polyhydric alcohols, and the like, thereby further producing unsaturated polyester resin, polyurethane, surface active agent, and fire retardant, and so on. Propylene oxide is widely used in the industries of chemical engineering, light manufacturing, pharmaceuticals, food, and textile, and has far-reaching influence on the development of chemical industry as well as the national economy. As the range of application of propylene oxide expands and the use amount of downstream product thereof increases, the market demand for propylene oxide is becoming higher and higher.

Currently, the main processes for the industrial manufacturing of propylene oxide include chlorohydrin process, co-oxidation process for propylene oxide with co-product (PO/SM process and PO/MTBE process or PO/TBA process), and cumyl hydroperoxide process for propylene oxide without co-product (CHP process). Because the chlorohydrin process produces large amount of chlorine-containing effluent in the manufacturing process, environmental pollution will be caused and the apparatus will be severely corroded. Co-oxidation process for propylene oxide with co-product can eliminate the defects of pollution and corrosion of the chlorohydrin process, but it also suffers from lengthy technological process, large investment, and large amount of co-products, which influence the manufacturing of propylene oxide to a certain extent. CHP process has become the development trend for the production technology of propylene oxide due to its light pollution level and free of co-product.

The technology for preparing propylene oxide compound from cumyl hydroperoxide (CHP) and propylene in the presence of fixed bed catalysts is known. Said technology mainly comprises three reaction steps. First, atmospheric oxidation of cumene takes place for preparing cumyl hydroperoxide. Then, an epoxidation reaction between CHP and propylene in the presence of heterogeneous catalysts takes place, and propylene oxide (PO) and α,α-dimethyl-benzyl alcohol (DMBA) are generated. Subsequently, hydrogenolysis reaction of DMBA with $H_2$ takes place in the presence of catalysts, and generates cumene, which is recirculated to the oxidation process for preparing CHP. In order to improve the conversion ratio of CHP, excessive amount of propylene is usually used. For example, the molar ratio of propylene to CHP is in a range of 5-20, thus there is excessive amount of propylene in the reaction product. In order to improve the epoxidation efficiency and reduce the load of PO refinement, it is required that the propylene in the reaction product be recycled. The circulating propylene should have high purity and be rid of impurities. In the meantime, the accumulation of inert components in the circulating system should be avoided.

According to literature CN1505616A, a process for preparing propylene oxide is proposed, comprising the following steps: first, propylene is reacted with cumyl hydroperoxide in the presence of catalysts, and propylene oxide is generated; then a reaction mixture obtained from the first step is distilled, and unreacted propylene is recycled from the distillation column. A bottom temperature of the distillation column is set at 200° C. or lower. According to the above process, crude PO product is obtained from the bottom of the distillation column and propylene is obtained from the top thereof. Due to the thermo sensitivity of PO, the temperature of the column bottom is generally controlled no higher than 130° C. during industrial production. That is, the operating pressure of the distillation column is defined, rendering the operating temperature at the top of the distillation column to be lower than 40° C. As a result, it is impossible to use conventional cooling water as the cryogen, but rather, large amount of cryogen of even lower temperature is required for the condensation recovery of propylene. Consequently, the industrial operation will be difficult and the power consumption will be high.

SUMMARY OF THE INVENTION

The present disclosure strives to solve technical problem of high power consumption in the prior art, and to provide a novel process and apparatus for recycling and refining propylene. According to the present disclosure, use of low temperature cryogen can be avoided. Therefore, the present disclosure has the advantages of high propylene recovery percent, complete propane removal, high yield of propylene oxide product, lower investment to the apparatus, simple process, and high industrial implementability, and the like.

A process for recycling and refining propylene is proposed according to the present disclosure, comprising the steps of:

step 1: feeding a stream containing propylene, cumene, α,α-dimethyl-benzyl alcohol, propane, and propylene oxide, which is obtained from an epoxidation reaction, to a first propylene recovery column, then obtaining a first light component stream containing non-condensable gas from a top of the first propylene recovery column, a first heavy component stream containing propylene, cumene, α,α-dimethyl-benzyl alcohol, and propylene oxide from a bottom thereof, and a side-draw stream containing propylene from an intermediate section thereof, and subsequently dividing the side-draw stream into a first side-draw stream and a second side-draw stream;

step 2: feeding the first side-draw stream to a depropanizing column, and obtaining a second light component stream from a top of the depropanizing column and a second heavy component stream containing propane from a bottom thereof;

step 3: performing a adiabatic flash separation on the first heavy component stream, and obtaining a third light component stream containing propylene, cumene, and propylene oxide, and a third heavy component stream containing α,α-dimethyl-benzyl alcohol, cumene, and propylene oxide; and step 4: feeding the third light component stream and the third heavy component stream to a second propylene recovery column, the position, through which the third heavy component is fed to the second propylene recovery column, being higher than the position, through which the third light component stream is fed thereto; then feeding a fourth light component stream, which contains propylene and is obtained from a top of the second propylene recovery column, to the first propylene recovery column, and obtaining a fourth heavy component stream containing propylene oxide, α,α-dimethyl-benzyl alcohol, and cumene from the bottom of the second propylene recovery column, wherein the second side-draw stream and the second light component stream are recovered propylene.

According to the present disclosure, the side-draw stream mainly contains propylene. In an embodiment, the fourth light component basically consists of propylene. Partial stream mainly containing propylene (the first side-draw stream) is fed to the depropanizing column to have the propane therein removed, so that the accumulation of inert impurity propane can be avoided. A liquid phase stream (i.e., the third heavy component stream) obtained from the adiabatic flashing separation is used in the second propylene recovery column as absorption liquid for the gas phase stream (i.e., the third light component stream), and the overhead gas phase of the second propylene recovery column is circulated back to the first propylene recovery column so as to recover propylene. In such a manner, the use of low temperature cryogen can be avoided. The propylene recovered from the first propylene recovery column is not from the top thereof, but rather from a side line thereof. In this way, gases (non-condensable gases), such as CO and $CO_2$, produced from the reaction can be removed, thus can be prevented from entering into the reaction system with the recovered propylene. As a result, the purity of the recovered propylene can be improved. That is, the non-condensable gases, which contain CO and $CO_2$, can be discharged or used for other purposes.

In an embodiment according to the present disclosure, a ratio of a weight of the first side-draw stream to that of the side-draw stream is in a range of (0.05-0.5):1, i.e., 1:(20-2). In an embodiment, the ratio of the weight of the first side-draw stream to that of the side-draw stream is in a range of 1:(8-15). The majority of the stream mainly containing propylene (the second side-draw stream) is recovered through the first propylene recovery column, and only a small amount of propylene is obtained from the top of the depropanizing column. The small amount of stream mainly containing propylene (the first side-draw stream) is fed to the depropanizing column to have the propane therein removed, so that the accumulation of inert impurity propane can be avoided.

In an embodiment according to the present disclosure, the third heavy component stream is fed to the first tray at the top of the second propylene recovery column, and the third light component stream is fed to an intermediate section thereof. In this case, the separation efficiency of the second propylene recovery column and the utilization ratio thereof can be improved, the use of low temperature cryogen can be avoided, and the power consumption can be reduced.

In another embodiment according to the present disclosure, in the stream containing propylene, cumene, α,α-dimethyl-benzyl alcohol, propane, and propylene oxide, calculated by weight percentage, the content of α,α-dimethyl-benzyl alcohol accounts for 19-50%, that of cumene accounts for 10-70%, that of propylene oxide accounts for 5-20%, that of propylene accounts for 5-60%, and that of propane accounts for 0-10%.

In another embodiment of the process according to the present disclosure, the stream containing propylene, cumene, α,α-dimethyl-benzyl alcohol, propane, and propylene oxide is obtained from products of the epoxidation reaction of industrial propylene and optional circulating propylene with cumyl hydroperoxide. Industrial propylene usually contains ethane and propane. Under such circumstances, by recovering propylene from a side line of the first propylene recovery column, impurities generated in the reaction, such as $CO/CO_2$, as well as light components brought in with the industrial propylene material, such as ethane, can not only be removed, but also be prevented from entering into the reaction system with the recovered propylene. In this case, the purity of the recovered propylene can be improved. In other words, the non-condensable gases at this moment contain light component gases, such as CO, $CO_2$, and ethane. The optional circulating propylene means that the stream can be with or without circulating propylene.

In another embodiment of the process according to the present disclosure, an operating pressure of the first propylene recovery column by gage pressure is in a range of 1.5-2.5 MPa. An operating pressure of the second propylene recovery column by gage pressure is in a range of 0.01-0.2 MPa. It is observed that the pressure of the first propylene recovery column is larger than that of the second propylene recovery column. Thus, the first propylene recovery column can also be called a high pressure propylene recovery column, and the second propylene recovery column can also be called a low pressure propylene recovery column. After being separated through the second propylene recovery column, the fourth heavy component stream basically contains no propylene. The fourth heavy component stream can be further separated, so that the propylene oxide can be purified.

In a further embodiment of the process according to the present disclosure, an operating pressure of the flash separation by gage pressure is in a range of 0.5-1.5 MPa, and an operating temperature thereof is in a range of 90-110° C.

In a further embodiment of the process according to the present disclosure, an operating pressure of the depropanizing column by gage pressure is in a range of 1.5-2.5 MPa, an operating temperature at a top thereof is in a range of 40-65° C., an operating temperature at a bottom thereof is in a range of 40-65° C., and a number of theoretical plates thereof is in a range of 10-80. A stream from the bottom of the depropanizing column, i.e., the second heavy component stream (propane containing stream), can be discharged.

In another embodiment of the process according to the present disclosure, an operating temperature at the top of the first propylene recovery column is in a range of 5-80° C., an operating temperature at the bottom thereof is in a range of 45-120° C., and a number of theoretical plates thereof is in a range of 10-50. An operating temperature at the top of the second propylene recovery column is in a range of 10-50° C., an operating temperature at the bottom thereof is in a range of 70-120° C., and a number of theoretical plates thereof is in a range of 10-50.

The stream can be better separated by means of controlling the technological parameters of the first and the second propylene recovery columns, those of the flash tank, and those of the depropanizing column. As a result, the propylene recovery percent, the yield of propylene oxide, as well as the purity of the recovered propylene can all be improved.

In another embodiment of the process according to the present disclosure, the propylene has high recovery percent (as high as 99.9%) and the recovered propylene has high purity (as high as 95%), thus can be used as circulating propylene to be reused. When the circulating propylene is reused in the process according to the present disclosure, the accumulation of impurity propane in the system can be avoided. The recovered propylene can be circulated to the epoxidation reaction system and participate in the epoxidation reaction.

In another embodiment of the process according to the present disclosure, the third heavy component stream is cooled, preferably to a temperature in a range of 10-50° C., and subsequently fed to the first tray at the top of the second propylene recovery column. The cooled third heavy component stream can play the role as absorption liquid better, so that the use of low temperature cryogen can be avoided.

In another embodiment of the process according to the present disclosure, the fourth light component stream is supercharged, and then fed to the bottom of the first propylene recovery column. Preferably, the fourth light component stream is cooled to a temperature in a range of 10-40° C., and then a gas phase-liquid phase separation is performed on the fourth light component stream, and subsequently the gas phase and the liquid phase are respectively supercharged and fed to the first propylene recovery column. In this case, the fourth light component stream, which basically contains propylene, is circulated back to the first propylene recovery column, so that propylene can be recovered from the second side-draw stream, thereby the use of low temperature cryogen can be avoided.

In another aspect of the present disclosure, an apparatus for recycling and refining propylene is provided, comprising:

a first propylene recovery column, wherein an inlet port of the first propylene recovery column is connected with a pipe for a stream containing propylene, cumene, α,α-dimethyl-benzyl alcohol, propane, and propylene oxide, an outlet port at a top thereof is connected with a pipe for a first light component stream, an outlet port at a bottom thereof is connected with a pipe for a first heavy component stream, and an outlet port at a side line of an intermediate section thereof is connected with a pipe for a side-draw stream, the pipe for the side-draw stream being communicated with a pipe for a first side-draw stream and a pipe for a second side-draw stream, and the first propylene recovery column is used for the separation of the stream containing propylene, cumene, α,α-dimethyl-benzyl alcohol, propane, and propylene oxide obtained from an epoxidation reaction, thereby obtaining a first light component stream containing non-condensable gas from the top of the first propylene recovery column, a first heavy component stream containing propylene, cumene, α,α-dimethyl-benzyl alcohol, and propylene oxide from the bottom thereof, and a side-draw stream containing propylene from the side line at the intermediate section thereof, the side-draw stream being divided into the first side-draw stream and the second side-draw stream;

a depropanizing column, wherein an inlet port at an intermediate section of the depropanizing column is connected with the pipe for the first side-draw stream, an outlet port at a top thereof is connected with a pipe for a second light component stream, and an outlet port at a bottom thereof is connected with a pipe for a second heavy component stream, and the depropanizing column is used for receiving and separating the first side-draw stream, which is from the pipe, thereby obtaining the second light component stream from the top of the depropanizing column, and the second heavy component stream containing propane from the bottom thereof;

a flash tank, wherein an inlet port of the flash tank is connected with the pipe for the first heavy component stream, an outlet port at a top thereof is connected with a pipe for a third light component stream, and an outlet at a bottom thereof is connected with a pipe for a third light component stream, and the flash tank is used for receiving and separating the first heavy component stream, which is from the bottom of the first propylene recovery column, thereby obtaining the third light component stream containing propylene, cumene, and propylene oxide from the top of the flash tank, and the third heavy component stream containing α,α-dimethyl-benzyl alcohol, cumene, and propylene oxide from the bottom thereof;

a second propylene recovery column, wherein inlet ports respectively connected with the pipe for the third light component stream and the pipe for the third heavy component stream are arranged on a middle-upper part of the second propylene recovery column, the inlet port connected with the pipe for the third heavy component stream being located at a higher position than the inlet port connected with the pipe for the third light component stream, an outlet port at the top of the second propylene recovery column is connected with a pipe for a fourth light component stream, and an outlet port at a bottom thereof is connected with a pipe for a fourth heavy component stream, the pipe for the fourth light component stream is communicated with the bottom of the first propylene recovery column, and the second propylene recovery column is used for receiving the third light component stream and the third heavy component stream from the flash tank, thereby obtaining the fourth light component stream containing propylene from the top of the second propylene recovery column, and the fourth heavy component stream containing propylene oxide, α,α-dimethyl-benzyl alcohol, and cumene from the bottom thereof, the fourth light component stream being circulated back to the bottom of the first propylene recovery column;

wherein the pipe for the second side-draw stream and the pipe for the second light component stream are used for recovering propylene.

According to the present disclosure, the side-draw stream mainly contains propylene. In an embodiment, the fourth light component stream contains basically propylene. Partial stream (the first side-draw stream), which mainly contains propylene, is fed to the depropanizing column to have the propane therein removed, so that the accumulation of inert impurity propane can be avoided. A liquid phase stream (i.e., the third heavy component stream) obtained from the adiabatic flashing separation is used in the second propylene recovery column as absorption liquid for the gas phase stream (i.e., the third light component stream), and the overhead gas phase of the second propylene recovery column is circulated back to the first propylene recovery column, so as to recover propylene. In such a manner, the use of low temperature cryogen can be avoided. The propylene is not recovered from the top of the first propylene recovery column, but rather from a side line thereof. In this way, gases such as CO and $CO_2$ (non-condensable gases) produced from the reaction can be removed, thus can be prevented from entering into the reaction system with the recovered propylene. As a result, the purity of the recovered propylene can be improved. That is, the non-condensable gases, which contain CO and $CO_2$, can be discharged or used for other purposes.

In an embodiment of the apparatus according to the present disclosure, an inlet of the pipe for the third light component stream is located at an intermediate section of the second propylene recovery column, and an inlet of the pipe for the third heavy component stream is located at a first tray at the top thereof, thereby feeding the third heavy component stream to the first tray at the top of the second propylene recovery column, and the third light component stream to the intermediate section thereof. With such arrangements, the separation efficiency of the second propylene recovery column and the utilization ratio thereof can be improved, the use of low temperature cryogen can be avoided, and the power consumption can be reduced.

In another embodiment of the apparatus according to the present disclosure, a ratio of a weight of the first side-draw stream to that of the side-draw stream is in a range of (0.05-0.5):1. In an embodiment, the ratio of the weight of the first side-draw stream to that of the side-draw stream is in a range of 1:(8-15). The majority of the stream mainly containing propylene (the second side-draw stream) is recovered through the first propylene recovery column, and only a small amount of propylene is obtained from the top of the depropanizing column. The small amount of the stream mainly containing propylene (the first side-draw stream) is fed to the depropanizing column to have the propane therein removed, so that the accumulation of inert impurity propane can be avoided In another embodiment of the apparatus according to the present disclosure, an operating temperature at the top of the first propylene recovery column is in a range of 5-80° C., an operating temperature at the bottom thereof is in a range of 45-120° C., and a number of theoretical plates thereof is in a range of 10-50. An operating temperature at the top of the second propylene recovery column is in a range of 10-50° C., an operating temperature at the bottom thereof is in a range of 70-120° C., and a number of theoretical plates thereof is in a range of 10-50. An operating pressure of the depropanizing column by gage pressure is in a range of 1.5-2.5 MPa, an operating temperature at a top thereof is in a range of 40-65° C., an operating temperature at a bottom thereof is in a range of 40-65° C., and a number of theoretical plates thereof is in a range of 10-80. The stream from the bottom of the depropanizing column, i.e., the second heavy component stream (propane containing stream), can be discharged from the system. An operating pressure of the flash tank by gage pressure is in a range of 0.5-1.5 MPa, and an operating temperature thereof is in a range of 90-110° C.

The stream can be better separated by means of controlling the technological parameters of the first and the second propylene recovery columns, those of the flash tank, and those of the depropanizing column. As a result, the propylene recovery percent, the yield of propylene oxide, as well as the purity of the recovered propylene can all be improved. After separation through the second propylene recovery column, the fourth heavy component stream basically contains no propylene. The fourth heavy component can be further separated, so that the propylene oxide can be purified.

In another embodiment of the apparatus according to the present disclosure, in the stream containing propylene, cumene, α,α-dimethyl-benzyl alcohol, propane, and propylene oxide, calculated by weight percentage, the content of α,α-dimethyl-benzyl alcohol accounts for 19-50%, that of cumene accounts for 10-70%, that of propylene oxide accounts for 5-20%, that of propylene accounts for 5-60%, and that of propane accounts for 0-10%.

In another embodiment of the apparatus according to the present disclosure, the stream containing propylene, cumene, α,α-dimethyl-benzyl alcohol, propane, and propylene oxide is obtained from products of reaction of industrial propylene and optional circulating propylene with cumyl hydroperoxide. Industrial propylene usually contains ethane and propane. Under such circumstances, by reovering propylene from a side line of the first propylene recovery column, impurities such as CO and $CO_2$ produced in the reaction, as well as light components, such as ethane brought in with the industrial propylene material, can not only be removed, but also be prevented from entering into the reaction system with the recovered propylene. In this case, the purity of the recovered propylene can be improved. In other words, the non-condensable gases at this moment contain light component gases, such as CO, $CO_2$, and ethane. The optional circulating propylene means that the stream can be with or without circulating propylene.

The recovered propylene has high purity thus can be used as circulating propylene to be reused. When the circulating propylene is reused in the process according to the present disclosure, the accumulation of impurity propane in the system can be avoided. The recovered propylene can be circulated to the epoxidation reaction system and participate in the epoxidation reaction.

In another embodiment of the apparatus according to the present disclosure, the apparatus further comprises a cooling device, so that the third heavy component stream can be cooled, preferably to a temperature in a range of 10-50° C., and subsequently fed to the first tray at the top of the second propylene recovery column. The cooled third heavy component stream can play the role as absorption liquid better, so that the use of low temperature cryogen can be avoided.

In another embodiment of the apparatus according to the present disclosure, the apparatus further comprises a supercharging device, so that the fourth light component stream can be supercharged and then fed to the bottom of the first propylene recovery column.

In another embodiment of the apparatus according to the present disclosure, the apparatus further comprises a cooling device and a compressor, so that the fourth light component stream can be cooled to a temperature in a range of 10-40° C. first, then a gas-liquid phase separation is performed on the fourth light component stream, and subsequently the gas phase is fed into the bottom of the first propylene recovery column after compressed by a compressor, and the liquid phase is supercharged and fed to the bottom of the first propylene recovery column. In such a manner, liquid can be prevented from being entrained into the compressor (and when the fourth light component stream contains traces of PO, polymerization reaction of thermosensitive substances, such as PO, can also be prevented). As a result, the stable and long term operation of the apparatus can be facilitated.

In another embodiment of the apparatus according to the present disclosure, a compression ratio of the compressor is in a range of 8-25, an exit pressure by gage pressure is in a range of 1.5-2.5 MPa, and an exit temperature is in a range of 10-120° C.

According to the present disclosure, the apparatus further comprises a compressor and a cooling device. The pipe for the third heavy component stream and/or the pipe for the fourth light component stream are/is connected with the cooling device, thereby feeding corresponding cooled stream to a subsequent process.

In the process and the apparatus according to the present disclosure, most propylene in the stream is recovered from the high pressure propylene recovery column, and only a small amount of propylene is recovered from the top of the depropanizing column. The propylene recovered from the high pressure propylene recovery column is not from the top, but rather from the side line of the propylene recovery column, so that impurities generated in the reaction, such as $CO/CO_2$, and light components brought in with the propylene material, such as ethane, can be removed. In this case, $CO/CO_2$ can be prevented from entering into the reaction system with the circulating propylene, and the purity of the circulating propylene can be improved. The low pressure propylene recovery column uses a liquid phase reaction product, on which an adiabatic flashing has been performed, as the absorption liquid for the gas phase. The overhead gas is preferably supercharged by the compressor first, and then circulated back to the high pressure propylene recovery column, so as to recover propylene. In this case, the use of low temperature cryogen can be avoided. The small amount of propylene is fed to the depropanizing column to have the propane therein removed, so that the inert impurity propane brought in with the propylene material can be prevented from being accumulated in the system. According to the process of the present disclosure, not only the power consumption can be reduced (by 70% as compared with the prior art), the recovery percent of propylene can also be guaranteed (as high as 99.9%). In the meantime, complete separation of propylene and the PO product can be realized, the requirement for the purity (up to 95%) of the circulating propylene can be met, and the yield (up to 99.9%) of the PO product can be guaranteed. The process according to the present disclosure can be applied to different technological processes for the propylene material, and has achieved favorable technical effects.

DETAILED DESCRIPTION OF THE EMBODIMENTS

Figure 1:
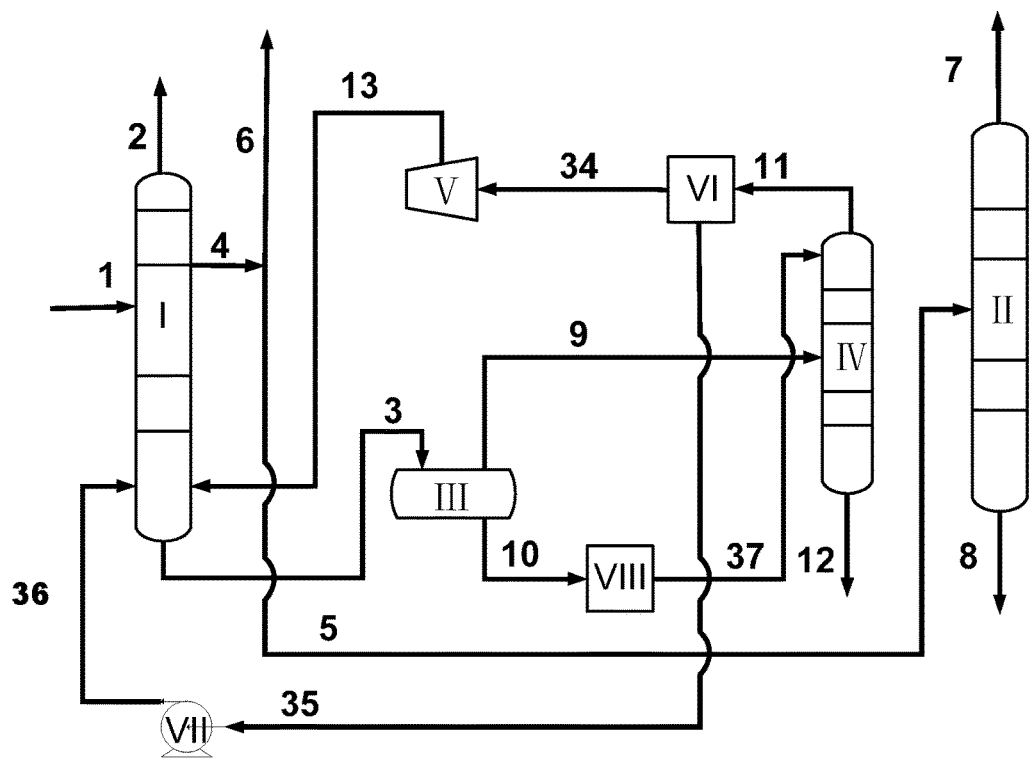
FIG. 1 schematically shows a technological process of an Example according to the present disclosure, and FIG. 2 schematically shows an apparatus of an Example according to the present disclosure.

Reference signs in FIG. 1 include:
I: first propylene recovery column,
II: depropanizing column,
III: flash tank,
IV: second propylene recovery column,
V: first compressor,
VI: first cooler,
VII: second compressor,
VIII: second cooler,
1: stream containing propylene, cumene, α,α-dimethyl-benzyl alcohol, propane, and propylene oxide,
2: first light component stream (an overhead stream from the first propylene recovery column, containing light components, such as CO, $CO_2$, ethane, and the like),
3: first heavy component stream (a stream at a bottom from the first propylene recovery column containing α,α-dimethyl-benzyl alcohol, cumene, propylene oxide, and propylene),
4: side-draw stream from the first propylene recovery column,
5: first side-draw stream,
6: second side-draw stream (propylene recovered from the first propylene recovery column),
7: second light component stream (propylene recovered from a top of the depropanizing column),
8: second heavy component stream (propane containing stream from a bottom of the depropanizing column),
9: third light component stream (gas phase stream from the flash tank containing large amount of propylene and small amount of propylene oxide and cumene),
10: third heavy component stream (liquid phase stream from the flash tank containing α,α-dimethyl-benzyl alcohol, cumene, propylene oxide, and small amount of propylene),
11: fourth light component stream (a stream from a top of the second propylene recovery column),
12: fourth heavy component stream (a stream of crude propylene oxide product from a bottom of the second propylene recovery column, containing α,α-dimethyl-benzyl alcohol, cumene, and propylene oxide),
13: supercharged fourth light component stream,
34: gas phase stream from a cooled fourth light component stream,
35: liquid phase stream from a cooled fourth light component stream,
36: supercharged liquid phase stream from a cooled fourth light component stream, and
37: cooled third heavy component stream.

As shown in FIG. 1, stream 1 is fed to an intermediate section of first propylene recovery column I, and propylene is recovered. The propylene obtained from the side line of first propylene recovery column I is divided into two portions. A major portion of propylene 6 is circulated back to an epoxidation reaction system (not shown) for reaction. A small portion of propylene 5 is fed to depropanizing column II to be refined. Heavy component stream 3 obtained from a bottom of First propylene recovery column I is fed to adiabatic flash tank III to be separated. Gas phase product 9 obtained from a top of adiabatic flash tank III is fed to an intermediate section of second propylene recovery column IV, and liquid phase product 10 obtained from a bottom of flash tank III is cooled by second cooler VIII, so as to generate cooled third heavy component stream 37. Cooled third heavy component stream 37 is fed to a first tray of second propylene recovery column IV as absorption liquid. Fourth light component stream 11 from the top of the second propylene recovery column IV is cooled by first cooler VI to form gas phase stream 34 and liquid phase stream 35. Gas phase stream 34 is supercharged by first compressor V, and then fed to the bottom of first propylene recovery column I. Liquid phase stream 35 is supercharged by second compressor VII and then fed to the bottom of first propylene recovery column I. Reaction product propylene oxide 12, which does not contain propylene and is obtained from the bottom of second propylene recovery column IV, is fed to a subsequent separation system. Propane 8 is removed from the bottom of depropanizing column II, and propylene 7 recovered from the top of depropanizing column II is circulated back to the epoxidation reaction system (not shown) for reaction.

Figure 2:
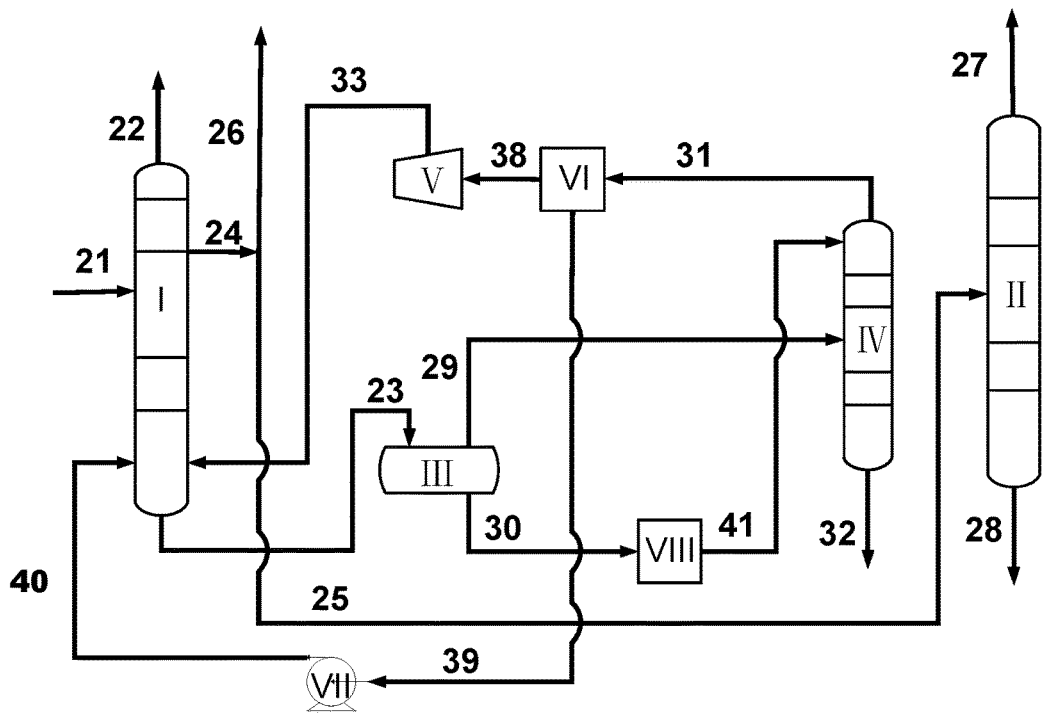

FIG. 2 schematically shows an apparatus according to the present disclosure. In FIG. 2, the reference signs include:
I: first propylene recovery column,
II: depropanizing column,
III: flash tank,
IV: second propylene recovery column,
V: first compressor,
VI: first cooler,
VII: second compressor, VIII: second cooler,
21: pipe for the stream containing propylene,
22: pipe for the first light component stream (containing therein an overhead stream from the first propylene recovery column containing light components, such as CO, $CO_2$, ethane, and the like),
23: pipe for the first heavy component stream (containing therein a stream from a bottom of the first propylene recovery column containing α,α-dimethyl-benzyl alcohol, cumene, propylene oxide, and propylene),
24: pipe for the side-draw stream from the first propylene recovery column,
25: pipe for the first side-draw stream,
26: pipe for the second side-draw stream (containing therein propylene recovered from the first propylene recovery column),
27: pipe for the second light component stream (containing therein propylene recovered from a top of the depropanizing column),
28: pipe for the second heavy component stream (containing therein propane containing stream from a bottom of the depropanizing column),
29: pipe for the third light component stream (containing therein gas phase stream from the flash tank containing large amount of propylene and small amount of propylene oxide and cumene),
30: pipe for the third heavy component stream (containing therein liquid phase stream from the flash tank containing α,α-dimethyl-benzyl alcohol, cumene, propylene oxide, and small amount of propylene),
31: pipe for the fourth light component stream (containing therein a stream from a top of the second propylene recovery column),
32: pipe for the fourth heavy component stream (containing therein a stream of crude propylene oxide product from a bottom of the second propylene recovery column, containing α,α-dimethyl-benzyl alcohol, cumene, and propylene oxide),
33: pipe for a stream from an outlet of the first compressor,
38: gas phase stream from a cooled fourth light component stream,
39: liquid phase stream from a cooled fourth light component stream,
40: supercharged liquid phase stream from a cooled fourth light component stream, and
41: cooled third heavy component stream.

As shown in FIG. 2, stream containing propylene passes through pipe 21 and is fed to the intermediate section of first propylene recovery column I. After separation, propylene obtained from the side line of the column is divided into two portions. The major portion of propylene is circulated back to the epoxidation reaction system (not shown) through pipe 26 for reaction, and the small portion of propylene is fed to depropanizing column II through pipe 25 to be refined. The heavy component stream obtained from the bottom of first propylene recovery column is fed to flash tank III through pipe 23 to be separated. Gas phase product obtained from the top of flash tank III is fed to the intermediate section of second propylene recovery column IV through pipe 29, and liquid phase product obtained from the bottom thereof is fed to second cooler VIII through the pipe 30 and then fed to the first tray through pipe 41 as absorption liquid for second propylene recovery column IV. Gas phase propylene from the top of second propylene recovery column IV is cooled by first cooler VI to form gas phase stream 38 and liquid phase stream 39. Gas phase stream 38 is supercharged by first compressor V, and then fed to the bottom of first propylene recovery column I through the pipe 33, and liquid phase stream 39 is surcharged by second compressor VII and then fed to the bottom of first propylene recovery column I through pipe 40 The reaction product propylene oxide, which does not contain propylene and is obtained from the bottom of second propylene recovery column IV, is fed to the subsequent separation system through pipe 32. Propane is removed from the bottom of depropanizing column II, and propylene recovered from the top of depropanizing column II is circulated back to the epoxidation reaction system (not shown) through pipe 27 for reaction.

Example 1

As shown in FIG. 1, a 100,000 ton/year PO apparatus is taken as an example. The stream containing α,α-dimethyl-benzyl alcohol, cumene, propylene oxide, propylene, and propane is from an epoxidation reaction system.

In the stream containing propylene, cumene, α,α-dimethyl-benzyl alcohol, propane, and propylene oxide, calculated by weight percentage, the content of α,α-dimethyl-benzyl alcohol is 26%, that of cumene is 6%, that of propylene oxide is 10%, that of propylene is 55%, and that of propane is 3%.

Operating conditions of the first propylene recovery column are as follows. An operating pressure by gage pressure is 2.0 MPa, an operating temperature at the top thereof is 48° C., an operating temperature at the bottom thereof is 102° C., and a number of theoretical plates thereof is 25.

Operating conditions of the second propylene recovery column are as follows. An operating pressure by gage pressure is 0.2 MPa, an operating temperature at the top thereof is 24° C., an operating temperature at the bottom thereof is 106° C., and a number of theoretical plates thereof is 20.

Operating conditions of the depropanizing column are as follows. An operating pressure by gage pressure is 2.0 MPa, an operating temperature at the top thereof is 51° C., an operating temperature at the bottom thereof is 56° C., and a number of theoretical plates thereof is 50.

A weight ratio of a stream 5 entering into the depropanizing column to the recovered propylene 6 is 1:13.

Operating conditions of the flash tank are as follows. An operating pressure by gage pressure is 0.7 MPa and an operating temperature is 77° C.

Operating conditions of the compressor are as follows. A compression ratio is 12, an exit pressure by gage pressure is 2.1 MPa, and an exit temperature is 124° C.

32° C. cooling water is applied at a rate of 608 ton/hr at the top of the first propylene recovery column as cryogen in the condensation and recovery of propylene. The compressor does 624 kw work.

A recovery percent of propylene is 99.9%, a purity of recovered propylene is 95%, and a yield of PO product is 99.9%. A recovery percent of propylene at the top of the first propylene recovery column is 92.5%.

Example 2

Example 2 is only different from example 1 in the contents of components in the stream containing α,α-dimethyl-benzyl alcohol, cumene, propylene oxide, propylene, and propane and the operating conditions.

In the stream containing α,α-dimethyl-benzyl alcohol, cumene, propylene oxide, propylene, and propane, calculated by weight percentage, the content of α,α-dimethylbenzyl alcohol is 26%, that of cumene is 21.5%, that of propylene oxide is 10.5%, that of propylene is 39%, and that of propane is 2%.

Operating conditions of the first propylene recovery column are as follows. An operating pressure by gage pressure is 1.8 MPa, an operating temperature at the top thereof is 45° C., an operating temperature at the bottom thereof is 124° C., and a number of theoretical plates thereof is 25.

Operating conditions of the second propylene recovery column are as follows. An operating pressure by gage pressure is 0.2 MPa, an operating temperature at the top thereof is 30° C., an operating temperature at the bottom thereof is 119° C., and a number of theoretical plates thereof is 20.

Operating conditions of the depropanizing column are as follows. An operating pressure by gage pressure is 2.0 MPa, an operating temperature at the top thereof is 51° C., an operating temperature at the bottom thereof is 57° C., and a number of theoretical plates thereof is 50.

A weight ratio of a stream 5 entering into the depropanizing column to the recovered propylene 6 is 1:9.

Operating conditions of the flash tank are as follows. An operating pressure by gage pressure is 0.7 MPa and an operating temperature is 106° C.

Operating conditions of the compressor are as follows. A compression ratio is 12, an exit pressure by gage pressure is 2.1 MPa, and an exit temperature is 124° C.

32° C. cooling water is applied at a rate of 467 ton/hr at the top of the first propylene recovery column as cryogen in the condensation and recovery of propylene. The compressor does 472 kw work.

A recovery percent of propylene is 99.9%, a purity of recovered propylene is 95%, and a yield of PO product is 99.9%. A recovery percent of propylene at the top of the first propylene recovery column is 92.5%.

Comparison Example 1

A same stream containing α,α-dimethyl-benzyl alcohol, cumene, propylene oxide, propylene, and propane as that in example 1 is fed to a distillation column. Unreacted propylene is recovered from a top of the distillation column, and crude PO product is obtained from a bottom thereof.

Operating conditions of the distillation column are as follows. An operating pressure is 0.3 MPa, an operating temperature at the top of the distillation column is −12° C., an operating temperature at the bottom thereof is 120° C., and a number of theoretical plates is 30.

As a result, −20° C. cryogen is used at the top of the distillation column at a rate of 92.5 ton/hr.

The invention claimed is:

1. A process comprising the steps of:
step 1: feeding a stream containing propylene, cumene, α,α-dimethyl-benzyl alcohol, propane, and propylene oxide, which is obtained from an epoxidation reaction, to a first propylene recovery column, then obtaining a first light component stream containing non-condensable gas from a top of the first propylene recovery column, a first heavy component stream containing propylene, cumene, α,α-dimethyl-benzyl alcohol, and propylene oxide from a bottom thereof, and a side-draw stream containing propylene from an intermediate section thereof, and subsequently dividing the side-draw stream into a first side-draw stream and a second side-draw stream;
step 2: feeding the first side-draw stream to a depropanizing column, and obtaining a second light component stream from a top of the depropanizing column and a second heavy component stream containing propane from a bottom thereof;
step 3: performing an adiabatic flash separation on the first heavy component stream, and obtaining a third light component stream containing propylene, cumene, and propylene oxide, and a third heavy component stream containing α,α-dimethyl-benzyl alcohol, cumene, and propylene oxide; and
step 4: feeding the third light component stream and the third heavy component stream to a second propylene recovery column, the position through which the third heavy component is fed to the second propylene recovery column being higher than the position through which the third light component stream is fed thereto; then feeding a fourth light component stream, which contains propylene and is obtained from a top of the second propylene recovery column, to the first propylene recovery column, and obtaining a fourth heavy component stream containing propylene oxide, α,α-dimethyl-benzyl alcohol, and cumene from the bottom of the second propylene recovery column,
wherein the second side-draw stream and the second light component stream are recovered propylene.

2. The process according to claim 1, wherein a ratio of a weight of the first side-draw stream to that of the side-draw stream is in a range of (0.05-0.5):1.

3. The process according to claim 1, wherein the third heavy component stream is fed to a first tray at the top of the second propylene recovery column, and the third light component stream is fed to an intermediate section thereof.

4. The process according to claim 1, wherein
in the stream containing propylene, cumene, α,α-dimethyl-benzyl alcohol, propane, and propylene oxide, calculated by weight percentage, the content of α,α-dimethyl-benzyl alcohol accounts for 19-50%, that of cumene accounts for 10-70%, that of propylene oxide accounts for 5-20%, that of propylene accounts for 5-60%, and that of propane accounts for 0-10%; and/or
the stream containing propylene, cumene, α,α-dimethyl-benzyl alcohol, propane, and propylene oxide is obtained from products of reaction of industrial propylene and optional circulating propylene with cumyl hydroperoxide; and/or
the recovered propylene is reused as the circulating propylene.

5. The process according to claim 1, wherein an operating pressure of the first propylene recovery column by gage pressure is in a range of 1.5-2.5 MPa, and/or an operating pressure of the second propylene recovery column by gage pressure is in a range of 0.01-0.2 MPa.

6. The process according to claim 1, wherein
an operating pressure of the adiabatic flash separation by gage pressure is in a range of 0.5-1.5 MPa, and an operating temperature thereof is in a range of 90-110° C.; and/or
an operating pressure of the depropanizing column by gage pressure is in a range of 1.5-2.5 MPa, an operating temperature at a top thereof is in a range of 40-65° C., an operating temperature at a bottom thereof is in a range of 40-65° C., and a number of theoretical plates thereof is in a range of 10-80.

7. The process according to claim 1, wherein
an operating temperature at the top of the first propylene recovery column is in a range of 5-80° C. an operating temperature at the bottom thereof is in a range of 45-120° C., and a number of theoretical plates thereof is in a range of 10-50; and/or an operating temperature at the top of the second propylene recovery column is in a range of 10-50° C., an operating temperature at the bottom thereof is in a range of 70-120° C., and a number of theoretical plates thereof is in a range of 10-50.

8. The process according to claim 3, wherein the third heavy component stream is cooled, preferably to a temperature in a range of 10-50° C., and subsequently fed to the first tray at the top of the second propylene recovery column.

9. The process according to claim 1, wherein the fourth light component stream is supercharged, and then fed to the bottom of the first propylene recovery column.

10. The process according to claim 1, wherein the fourth light component stream is cooled to a temperature in a range of 10-40° C., then a gas-liquid phase separation is performed on the fourth light component stream, and subsequently the gas phase and the liquid phase are supercharged respectively and fed to the first propylene recovery column.

11. An apparatus comprising:
a first propylene recovery column, wherein
an inlet port of the first propylene recovery column is connected with a pipe for a stream containing propylene, cumene, α,α-dimethyl-benzyl alcohol, propane, and propylene oxide, an outlet port at a top thereof is connected with a pipe for a non-condensable first light component stream, an outlet port at a bottom thereof is connected with a pipe for a first heavy component stream, and a side-draw outlet port at an intermediate section thereof is connected with a pipe for a side-draw stream, the pipe for the side-draw stream being communicated with a pipe for a first side-draw stream and a pipe for a second side-draw stream, and
the first propylene recovery column is configured for the separation of the stream containing propylene, cumene, α,α-dimethyl-benzyl alcohol, propane, and propylene oxide obtained from a epoxidation reaction, thereby obtaining the non-condensable first light component stream from the top of the first propylene recovery column, the first heavy component stream containing propylene, cumene, α,α-dimethyl-benzyl alcohol, and propylene oxide from the bottom thereof, and the side-draw stream comprising propylene from the side-draw outlet port at an intermediate section thereof, the side-draw stream being divided into the first side-draw stream and the second side-draw stream;
a depropanizing column, wherein
an inlet port at an intermediate section of the depropanizing column is connected with the pipe for the first side-draw stream, an outlet port at a top thereof is connected with a pipe for a second light component stream, and an outlet port at a bottom thereof is connected with a pipe for a second heavy component stream, and
the depropanizing column is configured for receiving and separating the first side-draw stream from the pipe for the first side-draw stream, thereby obtaining the second light component stream from the top of the depropanizing column, and the second heavy component propane containing stream from the bottom thereof;
a flash tank, wherein
an inlet port of the flash tank is connected with the pipe for the first heavy component stream, an outlet port at a top thereof is connected with a pipe for a third light component stream, and an outlet at a bottom thereof is connected with a pipe for a third light component stream, and the flash tank is configured for receiving and separating the first heavy component stream from the bottom of the first propylene recovery column, thereby obtaining the third light component stream containing propylene, cumene, and propylene oxide from the top of the flash tank, and the third heavy component stream containing α,α-dimethyl-benzyl alcohol, cumene, and propylene oxide from the bottom thereof;

a second propylene recovery column, wherein
inlet ports respectively connected with the pipe for the third light component stream and the pipe for the third heavy component stream are respectively arranged on a middle-upper part of the second propylene recovery column, the inlet port connected with the pipe for the third heavy component stream being located at a higher position than the inlet port connected with the pipe for the third light component stream,
an outlet port at the top of the second propylene recovery column is connected with a pipe for a fourth light component stream, and an outlet port at a bottom thereof is connected with a pipe for a fourth heavy component stream, and
the second propylene recovery column is configured for receiving the third light component stream and the third heavy component stream from the flash tank, thereby obtaining the fourth light component stream containing propylene from the top of the second propylene recovery column, the fourth heavy component stream containing propylene oxide, α,α-dimethyl-benzyl alcohol, and cumene from the bottom thereof, the fourth light component stream being recirculated back to the bottom of the first propylene recovery column;
wherein the pipe for the second side-draw stream and the pipe for the second light component stream are configured for providing recovered propylene.

12. The apparatus according to claim 11, wherein a ratio of a weight of the first side-draw stream to that of the side-draw stream is in a range of (0.05-0.5):1.

13. The apparatus according to claim 11, wherein
an operating temperature at the top of the first propylene recovery column is in a range of 5-80° C., an operating temperature at the bottom thereof is in a range of 45-120° C. and a number of theoretical plates thereof is in a range of 10-50; and/or
an operating temperature at the top of the second propylene recovery column is in a range of 10-50° C., an operating temperature at the bottom thereof is in a range of 70-120° C. and a number of theoretical plates thereof is in a range of 10-50, and/or
an operating pressure of the depropanizing column by gage pressure is in a range of 1.5-2.5 MPa, an operating temperature at a top thereof is in a range of 40-65° C., an operating temperature at a bottom thereof is in a range of 40-65° C., and a number of theoretical plates thereof is in a range of 10-80, and/or
an operating pressure of the flash tank by gage pressure is in a range of 0.5-1.5 MPa, and an operating temperature thereof is in a range of 90-110° C.

14. The apparatus according to claim 11, wherein an inlet of the pipe for the third light component stream is located at an intermediate section of the second propylene recovery column, and an inlet of the pipe for the third heavy component stream is located at a first tray at the top thereof, thereby feeding the third heavy component stream to the first tray at the top of the second propylene recovery column, and the third light component stream to the intermediate section thereof.

15. The apparatus according to claim 11, wherein in the stream containing propylene, cumene, α,α-dimethyl-benzyl alcohol, propane, and propylene oxide, calculated by weight percentage, the content of α,α-dimethyl-benzyl alcohol accounts for 19-50%, that of cumene accounts for 10-70%, that of propylene oxide accounts for 5-20%, that of propylene accounts for 5-60%, and that of propane accounts for 0-10%.

16. The apparatus according to claim 11, wherein
the stream containing propylene, cumene, α,α-dimethylbenzyl alcohol, propane, and propylene oxide is obtained from products of reaction of industrial propylene and optional circulating propylene with cumyl hydroperoxide; and/or
the recovered propylene is reused as the circulating propylene.

17. The apparatus according to claim 11, wherein the apparatus further comprises a cooling device, so that the third heavy component stream is cooled, preferably to a temperature in a range of 10-50° C., and subsequently fed to a first tray at the top of the second propylene recovery column.

18. The apparatus according to claim 11, wherein the apparatus further comprises a supercharging device, so that the fourth light component stream is supercharged and then fed to the first propylene recovery column.

19. The apparatus according to claim 18, wherein the apparatus further comprises a cooling device and a compressor, so that the fourth light component stream is cooled to a temperature in a range of 10-40° C. first, then a gas-liquid phase separation is performed on the fourth light component stream, and subsequently the gas phase is fed into the bottom of the first propylene recovery column after compressed by a compressor, and the liquid phase is supercharged and fed to the bottom of the first propylene recovery column.

20. The apparatus according to claim 19, wherein a compression ratio of the compressor is in a range of 8-25, an exit pressure by gage pressure is in a range of 1.5-2.5 MPa, and an exit temperature is in a range of 10-120° C.

* * * * *